(12) United States Patent
Youssef et al.

(10) Patent No.: US 11,045,406 B2
(45) Date of Patent: Jun. 29, 2021

(54) CLEAR SULFATE-FREE SURFACTANT BASED CLEANSER COMPOSITION WITH THICKENER

(71) Applicant: L'OREAL, Paris (FR)

(72) Inventors: Sara Robyn Muenz Youssef, Middlesex, NJ (US); Kelly Marie George, Denville, NJ (US); Carol Ragai Elmasry, South Amboy, NJ (US); Allison Elder, North Plainfield, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/907,436

(22) Filed: Feb. 28, 2018

(65) Prior Publication Data

US 2019/0262248 A1 Aug. 29, 2019

(51) Int. Cl.
| | | |
|---|---|---|
| *A61K 8/44* | (2006.01) | |
| *A61K 8/34* | (2006.01) | |
| *A61K 8/37* | (2006.01) | |
| *A61K 8/86* | (2006.01) | |
| *A61K 8/46* | (2006.01) | |
| *A61Q 5/12* | (2006.01) | |
| *A61Q 5/02* | (2006.01) | |
| *A61K 8/60* | (2006.01) | |
| *A61K 8/04* | (2006.01) | |
| *A61K 8/39* | (2006.01) | |
| *A61Q 19/10* | (2006.01) | |
| *A61K 8/87* | (2006.01) | |

(52) U.S. Cl.
CPC .............. *A61K 8/442* (2013.01); *A61K 8/042* (2013.01); *A61K 8/345* (2013.01); *A61K 8/37* (2013.01); *A61K 8/39* (2013.01); *A61K 8/44* (2013.01); *A61K 8/466* (2013.01); *A61K 8/608* (2013.01); *A61K 8/86* (2013.01); *A61K 8/87* (2013.01); *A61Q 5/02* (2013.01); *A61Q 5/12* (2013.01); *A61Q 19/10* (2013.01); *A61K 2800/262* (2013.01); *A61K 2800/28* (2013.01); *A61K 2800/596* (2013.01)

(58) Field of Classification Search
CPC .... A61K 8/39; A61K 2800/596; A61K 8/608; A61K 2800/28; A61K 8/345; A61K 8/466; A61K 2800/26
See application file for complete search history.

(56) References Cited

U.S. PATENT DOCUMENTS

| | | | |
|---|---|---|---|
| 8,865,147 B2 | 10/2014 | Rizk et al. | |
| 2004/0259744 A1* | 12/2004 | Yang | A61K 8/23 510/127 |
| 2006/0115442 A1 | 6/2006 | Katz et al. | |
| 2006/0217283 A1* | 9/2006 | De Salvert | A61K 8/046 510/417 |
| 2016/0095804 A1 | 4/2016 | Xavier et al. | |

FOREIGN PATENT DOCUMENTS

| | | |
|---|---|---|
| WO | 2015086608 A1 | 6/2015 |
| WO | WO-2015086608 A1 * | 6/2015 |

OTHER PUBLICATIONS

Mintel; Sep. 1, 2017, anonymous: "Cleansing Face Soap" XP55579238, retrieved from www.gnpd.com.
Mintel; Jan. 19, 2018, anonymous: "Sulfate Free Shampoo" XP55579284, retrieved from www.gnpd.com.
Mintel; Jul. 27, 2012, anonymous: "Shower Gel" XP55580208, retrieved from www.gnpd.com.
U. Kortemeier, U. Westerholt, P. Schwab, S. Langer, A. Howe: SOFW-Journal, vol. 140, 2014, pp. 2-10, XP002790527.
Dr. Samuel Lin, Applechem Inc.: "SorbiThix L-100—A New Generation of Liquid Non-Ionic Associative Thickener for Modern Personal Cleansing Formulations", In cosmetics Apr. 4-6, 2017, pp. 1-21, XP002790535.
PCT/US2019/019999 International Search Report dated Apr. 30, 2019.

* cited by examiner

*Primary Examiner* — Jianfeng Song
(74) *Attorney, Agent, or Firm* — McNees Wallace & Nurick LLC

(57) ABSTRACT

A cosmetic composition and a method of preparing the cosmetic composition are provided. The method includes mixing at least one sulfate-free surfactant, at least one thickener, at least one hydrophilic emollient to form a mixture; and adding solvent to the mixture. The cosmetic composition is a clear, flowable semi-solid, and converts to a non-flowable semi-solid upon rubbing.

2 Claims, No Drawings

CLEAR SULFATE-FREE SURFACTANT BASED CLEANSER COMPOSITION WITH THICKENER

FIELD OF THE INVENTION

The present invention is generally directed to a cosmetic composition and a method for preparing the cosmetic composition. More particularly, the present invention is directed to a cosmetic composition comprising at least one sulfate-free surfactant, at least one thickener, and at least one hydrophilic emollient, and a method for preparing the cosmetic composition.

BACKGROUND OF THE INVENTION

Cosmetic cleansing and shampoo formulations often contain sulfate-based surfactants such as sodium lauryl sulfate, sodium laureth sulfate, and ammonium laureth sulfate. These sulfate-based surfactants facilitate the cleansing process by decreasing: the surface tension of water and thus allowing water to adhere to the dirt on the skin or hair. However, sulfate-based surfactants have a tendency of making the skin or hair too dry and, therefore, consumers prefer to use products that don't contain sulfate-base surfactants. But, sulfate-free cleansers are difficult to thicken sufficiently to afford the good sensory properties. Such cleansers do not remain on the hair or skin during and/or after application, and can drip and run into the user's eyes, mouth, ears or nasal passages. This lends to an unpleasant consumer experience. Currently two approaches are employed to thicken sulfate-free cleanser formulas. One involves using high levels of non-sulfate surfactants to benefit from the self-assembling properties of such ingredients. This approach is most common, but it is also costly. The second approach involves using high levels of rheology modifiers; however, these components can adversely impact the properties of the composition by decreasing the foaming and ease of distribution of the composition. Thus, the current solutions for avoiding sulfate-based surfactants introduce one or more of excessive cost and loss of aesthetic and functional properties in a cosmetic cleanser.

Therefore, it is an object of the present invention to create a cleansing product that is free from sulfates, particularly sulfate-based surfactants, and also overcome the shortcomings in the art. This disclosure provides such a cleanser that is free of sulfates, particularly sulfate-based surfactants, and has pleasant aesthetics when applied to the skin. The cleanser is clear in appearance prior to application, and exhibits a unique textural transformation from a clear, flowable semi-solid to a non-flowable semi-solid upon rubbing. The composition provides not only an aesthetically appealing attribute upon application, but also advantageously remains in place on the keratinous surface to which it is applied so that it does not drip or run.

BRIEF DESCRIPTION OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

In an exemplary embodiment, a cosmetic composition is provided. The cosmetic composition includes at least one sulfate-free surfactant, at least one thickener, and at least one hydrophilic emollient. The cosmetic composition is a clear, flowable semi-solid, and converts to a non-flowable semi-solid upon rubbing. In some embodiments, the composition is completely free of sulfates. In some embodiments, the composition includes two or more of each of sulfate-free surfactants, thickeners, and hydrophilic emollients.

In another exemplary embodiment, a cleansing cosmetic composition is provided. The cosmetic composition includes from about 10 to about 30 wt % of at least one sulfate-free surfactant; from about 1 to about 20 wt % of at least one thickener; and from about 0.1 to about 5 wt % of at least one hydrophilic emollient. The composition also includes from about 50 to about 70 wt % of solvent. The cleansing cosmetic composition is a clear, flowable semi-solid, and converts to a non-flowable semi-solid upon rubbing.

In some particular embodiments, the at least one sulfate-free surfactant is selected from the group consisting of Disodium Laureth Sulfosuccinate (and) Sodium Lauryl Sulfoacetate, Coco-Betaine, Sodium Lauroyl Sarcosinate, and combinations thereof; the at least one thickener is selected from the group consisting of PEG-120 Methyl Glucose Trioleate, Propylene Glycol (And) PEG-55 Propylene Glycol Oleate, Steareth-100/PEG-136/HDI Copolymer, and combinations thereof; the at least one hydrophilic emollient is selected from the group consisting of PEG-7 Glyceryl Cocoate. In accordance with some embodiments, the solvent is water.

In another exemplary embodiment, a method of preparing a cosmetic composition is provided. The method includes mixing at least one sulfate-free surfactant, at least one thickener, and at least one hydrophilic emollient to form a mixture; and adding solvent to the mixture. The cosmetic composition is a clear, flowable semi-solid, and converts to a non-flowable semi-solid upon rubbing.

These and other aspects of the invention are set out in the appended claims, and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

As used herein, the term "sulfate-free surfactant" means free of anionic alkyl sulfates and alkyl ether sulfates. The terms "essentially free of sulfate-based surfactant" and "essentially sulfate free" refer to the contents of sulfate-based surfactants in the composition of the present invention. "Essentially free of sulfate-based surfactant" means that, while it prefers that no sulfate-based surfactants be present in the composition, it is possible to have very small amounts of sulfate-based surfactants in the composition of the invention, provided that these amounts do not materially affect the advantageous properties of the composition. In particular, "essentially free of sulfate-based surfactant" means that the sulfate-based surfactants can be present in the composition at an amount of less than about 2.0% by weight, typically less than about 1.5% by weight, typically less than about 1.0% by weight, typically less than about 0.5% by weight, typically less than about 0.1% by weight, and more typically 0% by weight, based on the total weight of the composition. The term "sulfate-based surfactant" as used herein, also means "sulfate-containing surfactant". Thus, the term "essentially free of sulfate-based surfactant" also means "essentially free of sulfate-containing surfactant".

As used herein, the term "clear" means the composition is translucent or transparent, not hazy or not opaque.

As used herein, the term "flowable" means the composition behaves like honey and has thick viscosity and slower flow response when pouring from a container.

As used herein, the term "non-flowable" means when external forces are applied to the composition, memory shape transformation starts and upon application to the surface of treated keratinous tissue, the composition stays put and does not drip.

In various embodiments, provided is a cosmetic cleansing composition that comprises a combination of at least one sulfate-free surfactant, at least one thickener and at least one hydrophilic emollient. The composition prior to application provides a flowable semi-solid cleanser that is clear in appearance. It was surprisingly discovered that the composition exhibits a unique and beneficial transformation upon rubbing, whereupon, it forms a non-flowable semi-solid that resists dripping and running off the surface of treated keratinous tissue. The unique transforming property provides an aesthetically appealing attribute upon application, and conversion to a non-flowable semi-solid ensures that the composition remains in place, making it particularly suitable for use on the face, in particular for use as a cleansing mask, even more particularly for in a shower type of application. The composition also demonstrates substantial performance as a cleanser, in particular for removing makeup from facial skin.

In some embodiments, a method of preparing a cosmetic composition is provided. The method includes mixing at least one sulfate-free surfactant, at least one thickener, and at least one hydrophilic emollient to form a mixture. The cosmetic composition is a clear, flowable semi-solid, and converts to a non-flowable semi-solid upon rubbing.

In some embodiments, the cosmetic composition is initially clear in appearance and remains clear in appearance upon application onto a keratinous substrate until rubbing, whereupon it forms a non-flowable semi-solid.

Sulfate-Free Surfactant

In accordance with the disclosure, at least one sulfate-free surfactant is present in the cosmetic composition. In some embodiments, the composition comprises two or more sulfate-free surfactants.

In accordance with some embodiments, sulfate-free surfactants may be selected from surfactants that form a clear composition that transforms to a non-flowable semi-solid and demonstrates cleansing and makeup removability and rinsability.

In some embodiments, the at least one sulfate-free surfactant is selected from Disodium Laureth Sulfosuccinate (and) Sodium Lauryl Sulfoacetate, Coco-Betaine and combinations thereof. In some embodiments, the composition comprises Disodium Laureth Sulfosuccinate (and) Sodium Lauryl Sulfoacetate and Coco-Betaine. Although these sulfate-free surfactants are given as an example, it will be appreciated that other sulfate-free surfactants compatible with cosmetic applications known in the art may be used.

In accordance with the various embodiments, the amount of sulfate-free surfactant present in the composition can range from about 1.5% to about 35%. In some embodiments, each of one or more sulfate-free surfactants may be present in an amount from about 1.5% to about 30%, from about 2% to about 25%, from about 3% to about 20%, from about 4% to about 15%, from about 5% to about 10% or any suitable combination, sub-combination, range, or sub-range thereof by weight, based on the total weight of the composition. In some embodiments, a combination of two or more sulfate-free surfactants may be present in a combined amount from about 10% to about 35%, from about 3% to about 30%, from about 6% to about 28%, or any suitable combination, sub-combination, range, or sub-range thereof by weight, based on the total weight of the composition. One of ordinary skill in the art, however, will appreciate that other ranges are within the scope of the invention. In some embodiments, two or more sulfate-free surfactants are present.

Thickener

In accordance with the disclosure, at least one thickener is present in the cosmetic composition. In some embodiments, the composition comprises two or more thickeners. In accordance with some embodiments, at least one thickener is selected from synthetic polymeric thickeners. In some embodiments, at least one thickener is selected from thickeners that form a clear composition that transforms to a non-flowable semi-solid and demonstrates cleansing, makeup removability and rinsability.

In accordance with the disclosure, the at least one thickener present in the cosmetic composition includes, but is not limited to, Propylene Glycol (and) PEG-55 Propylene Glycol Oleate, steareth-100/PEG-136/HDI copolymer, PEG-120 methyl glucose trioleate, and combinations thereof. Although these thickeners are given as an example, it will be appreciated that other thickeners compatible with cosmetic applications known in the art may be used.

In accordance with the various embodiments, the amount of thickener present in the composition can range from about 1% to about 25%. In some embodiments, each of one or more thickener may be present in an amount from about 1% to about 25%, from about 2% to about 20%, from about 3% to about 15%, 4% to about 10% or any suitable combination, sub-combination, range, or sub-range thereof by weight, based on the total weight of the composition. In some embodiments, a combination of two or more thickeners may be present in a combined amount from about 1% to about 25%. One of ordinary skill in the art, however, will appreciate that other ranges are within the scope of the invention. In some embodiments, two or more thickeners are present.

Hydrophilic Emollient

In accordance with the disclosure, the at least one hydrophilic emollient is present in the cosmetic composition. In some embodiments, the composition comprises two or more hydrophilic emollients. In some embodiments, the at least one hydrophilic emollient is selected from emollients that form a clear composition that transforms to a non-flowable semi-solid texture and demonstrates ease of application, spreadability without greasiness, cleansing, makeup removability and rinsability.

In accordance with the disclosure, the at least one hydrophilic emollient that is present in the composition is PEG-7 Glyceryl Cocoate.

In accordance with the various embodiments, the amount of hydrophilic emollient present in the composition can range from about 0.1% to about 10%. In some embodiments, each of one or more hydrophilic emollients may be present in an amount from about 0.1% to about 10%, from about 0.5% to about 5%, from about 1% to about 2%, or any suitable combination, sub-combination, range, or sub-range thereof by weight, based on the total weight of the composition. In some embodiments, a combination of two or more hydrophilic emollients may be present in a combined amount from about 1% to about 25%. One of ordinary skill in the art, however, will appreciate that other ranges are within the scope of the invention. In some embodiments, two or more hydrophilic emollients are present.

Solvent

In accordance with the disclosure, one or more solvents is present in the cosmetic composition, including, but not limited to, water, caprylyl glycol, and combinations thereof. Although these solvents are given as an example, it will be appreciated that other solvents compatible with cosmetic applications known in the art may be used. In accordance with the various embodiments, the solvent is present in a given composition in an amount of from about 50% to about 70% by weight, of from about 51% to about 69% by weight, of from about 52% to about 68% by weight, of from about 53% to about 67% by weight, of from about 54% to about 66% by weight, of from about 55% to about 65% by weight, of from about 56% to about 64% by weight, of from about 57% to about 63% by weight, of from about 58% to about 62% by weight, of from about 59% to about 61% by weight, or any suitable combination, sub-combination, range, or sub-range thereof by weight, based upon the total weight of the composition. One of ordinary skill in the art, however, will appreciate that other ranges are within the scope of the invention.

Optional Components

In accordance with the various embodiments, there may be one or more actives present in the cosmetic composition, according to the disclosure, including, but not limited to: humectants, such as acetamide MEA, glycols, such as glycerin and propylene glycol; alcohol; anti-microbial components, such as zinc pyrrolidone carboxylic acid; salicylic acid; alpha hydroxy acid; anti-oxidant compounds, including, phenolic compounds, such as chalcones, flavones, flavanones, flavanols, flavonols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, and phenolic terpenes, resveratrol, curcumin, pinoresinol, ferulic acid, hydroxytyrosol, cinnamic acid, caffeic acid, p-coumaric acid, baicalin (*Scutellaria baicalensis* root extract), pine bark extract (*Pinus pinaster* bark/bud extract), ellagic acid; anti-acne compounds; anti-aging compounds; and vitamins and vitamin derivatives, such as panthenol, ascorbic acid; and combinations thereof.

In some embodiments, there may be one or more other components present in the cosmetic composition, according to the disclosure, including, but not limited to, preservatives, vitamins, antimicrobials, fillers, such as clays, talc, penetrants; sequestrants; fragrances; dispersants; film-forming agents; ceramides; and combinations thereof.

In some embodiments, the optional components function as a base for actives.

Although the aforementioned optional components are given as an example, it will be appreciated that other optional components compatible with cosmetic applications known in the art may be used.

In accordance with the various embodiments, the amount of actives and other components present in the composition can range from about 0% to about 50%, from about 0.5% to about 30%, from about 1.5% to about 20%, and from about 5% to about 15%.

In some embodiments, one or more actives, alone or in combination, can be present in the composition according to the disclosure from about 0.05% to about 50% by weight, from about 0.05% to about 2.5% by weight, from about 0.1% to about 2% by weight, from about 0.25% to about 1.5% by weight, and from about 0.5% to about 1.25% by weight, with respect to the total weight of the composition.

In some embodiments, one or more other components can be present in the composition according to the disclosure from about 0.05% to about 50% by weight, from about 0.05% to about 25% by weight, from about 0.1% to about 10% by weight, from about 0.25% to about 5% by weight, and from about 0.5% to about 3.5% by weight, with respect to the total weight of the composition.

Examples

The following examples illustrate the present invention but are not intended to limit the scope of the invention.

TABLE 1

| | | Inventive compositions | | |
|---|---|---|---|---|
| COMPONENT | INCI US | Inventive composition 1 | Inventive composition 2 | Inventive composition 3 |
| CHELATING AGENT | TRISODIUM ETHYLENEDIAMINE DISUCCINATE | 0.5 | 0.5 | 0.5 |
| THICKENER | PROPYLENE GLYCOL (and) PEG-55 PROPYLENE GLYCOL OLEATE | | 15 | |
| THICKENER | STEARETH-100/PEG-136/HDI COPOLYMER | | | 2.5 |
| THICKENER | PEG-120 METHYL GLUCOSE TRIOLEATE | 12.5 | | |
| PRESERVATIVE | SALICYLIC ACID AND PHENOXYETHANOL | 0.9 | 0.9 | 0.9 |
| SOLVENT/ ANTIMICROBIAL | CAPRYLYL GLYCOL | 0.3 | 0.3 | 0.3 |
| SURFACTANT | COCO-BETAINE | 5 | 5 | 5 |
| SURFACTANT | DISODIUM LAURETH SULFOSUCCINATE (and) SODIUM LAURYL SULFOACETATE | 22.5 | 22.5 | 22.5 |

TABLE 1-continued

Inventive compositions

| COMPONENT | INCI US | Inventive composition 1 | Inventive composition 2 | Inventive composition 3 |
|---|---|---|---|---|
| EMOLLIENT | PEG-7 GLYCERYL COCOATE | 1.05 | 1.05 | 1.05 |
| SOLVENT | WATER | 57.25 | 54.75 | 67.25 |
| | SEMI-SOLID TEXTURE | YES | YES | YES |
| | EASE OF APPLICATION | EASY | EASY | EASY |
| | CLARITY | YES | YES | YES |

TABLE 2

Comparative compositions

| COMPONENT | INCI US | Comparative composition 1 | Comparative composition 2 | Comparative composition 3 | Comparative composition 4 |
|---|---|---|---|---|---|
| CHELATING AGENT | TRISODIUM ETHYLENEDIAMINE DISUCCINATE | 0.5 | 0.5 | 0.5 | 0.5 |
| THICKENER | PROPYLENE GLYCOL (and) PEG-55 PROPYLENE GLYCOL OLEATE | | | | |
| THICKENER | STEARETH-100/PEG-136/HDI COPOLYMER | | 3 | | |
| THICKENER | PEG-120 METHYL GLUCOSE TRIOLEATE | 15 | | | 7.5 |
| THICKENER | CETYL HYDROXYETHYL CELLULOSE | | | 2 | |
| PRESERVATIVE | SALICYLIC ACID AND PHENOXYETHANOL | 0.9 | 0.9 | 0.9 | 0.9 |
| SOLVENT/ ANTIMICROBIAL | CAPRYLYL GLYCOL | 0.3 | 0.3 | 0.3 | 0.3 |
| SURFACTANT | COCO-BETAINE | 3.33 | 5 | 5 | 7.5 |
| SURFACTANT | SODIUM LAUROYL SARCOSINATE | 3.33 | | | |
| SURFACTANT | DISODIUM LAURETH SULFOSUCCINATE (and) SODIUM LAURYL SULFOACETATE | 22 | 22.5 | 22.5 | 15 |
| EMOLLIENT | PEG-7 GLYCERYL COCOATE | | 1.05 | 1.05 | 1.8 |
| SOLVENT | WATER | 54.64 | 66.75 | 67.75 | 66.50 |
| | SEMI-SOLID TEXTURE | YES | NO | YES | NO |
| | EASE OF APPLICATION | DIFFICULT | EASY | EASY | EASY |
| | CLARITY | YES | YES | NO | YES |

Raw Materials

Compositions and formulations as described in the representative embodiments herein are selected from commercially available materials, including, for example, Thickeners: Glucamate LT Thickener from LUBRIZOL (INCI Name: PEG-120 Methyl Glucose Trioleate at 12.5%), Rheoluxe 811 from ELEMENTIS (INCI Name: Steareth-100/PEG-136/HDI Copolymer at 2.5%), Antil 141 Liquid from EVONIK GOLDSCHMIDT (INCI Name: Propylene Glycol (and) PEG-55 Propylene Glycol Oleate at 15.0%)/Surfactants: Stepan-Mild LSB from STEPAN (INCI Name: Disodium Laureth Sulfosuccinate (and) Sodium Lauryl Sulfoacetate), Coco-Betaine/Hydrophilic Emollient: PEG-7 Glyceryl Cocoate.

In some embodiments, a method of preparing a cosmetic composition is provided. The method includes mixing at least one sulfate-free surfactant, at least one thickener, at least one active compound to form a mixture; and adding a solvent to the mixture. The cosmetic composition is a clear, flowable semi-solid, and converts to a non-flowable semi-solid upon rubbing.

According to another embodiment of the invention, a method of cleansing and conditioning hair includes the steps of: (a) providing a composition for cleansing keratinous tissue having at least one sulfate-free surfactant, at least one thickener, and at least one hydrophilic emollient; (b) applying the composition to the skin or hair of a use until the composition transforms from a clear, flowable semi-solid to a non-flowable semi-solid; and, (c) rinsing the treated hair with a sufficient amount of water.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include sub-ranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cleansing cosmetic composition consisting of:
   sulfate-free surfactants consisting of Disodium Laureth Sulfosuccinate (and) Sodium Lauryl Sulfoacetate and Coco-Betaine present in a combined amount from about 6% to about 28% by weight based on the total weight of the composition, the Coco-Betaine being present in the composition in an amount from about 3% to about 20% by weight, based on the total weight of the composition;
   from about 1% to about 25 wt % of at least one thickener selected from the group consisting of Propylene Glycol (and) PEG-55 Propylene Glycol Oleate, steareth-100/PEG-136/HDI copolymer, PEG-120 methyl glucose trioleate, and combinations thereof;
   from about 1% to about 2% of at least one hydrophilic emollient comprising PEG-7 Glyceryl Cocoate;
   from about 50% to about 70 wt % of solvent selected from the group consisting of water, caprylyl glycol, and combinations thereof; and
   optionally, one or more additional components selected from the group consisting of a/n: actives selected from a/n humectant, antimicrobial, antioxidant, preservative, vitamin, vitamin derivative; and a/n filler, penetrant, fragrance, dispersant, film-forming agent; ceramide; anti-acne, anti-aging, and combinations thereof,
   wherein the cosmetic composition is a clear, flowable semi-solid, and converts to a non-flowable semi-solid upon rubbing.

2. The composition of claim 1, wherein each sulfate-free surfactant is present from about 2% to about 25% by weight, and wherein the at least one thickener comprises one or more of: PEG-120 methyl glucose trioleate present from about 3% to about 15% by weight, steareth-100/PEG-136/HDI copolymer present from about 2% to about 20% by weight, and Propylene Glycol (and) PEG-55 Propylene Glycol Oleate present from about 2% to about 20% by weight, all weights based on the total weight of the composition.

* * * * *